United States Patent
Cai et al.

(10) Patent No.: US 10,755,812 B1
(45) Date of Patent: Aug. 25, 2020

(54) SYSTEM AND METHOD FOR TIMELY NOTIFICATION OF TREATMENT

(71) Applicant: IMS Health Incorporated, Danbury, CT (US)

(72) Inventors: Yong Cai, Bala Cynwyd, PA (US); Bob Doyle, Wayne, PA (US); George Mu, Collegeville, PA (US); Dong Dai, Dresher, PA (US); Emily Zhao, Wayne, PA (US); Steven Rosztoczy, Warrington, PA (US)

(73) Assignee: IQVIA Inc., Parsippany, NJ (US)

( * ) Notice: Subject to any disclaimer, the term of this patent is extended or adjusted under 35 U.S.C. 154(b) by 1178 days.

(21) Appl. No.: 14/815,025

(22) Filed: Jul. 31, 2015

(51) Int. Cl.
*G16H 40/20* (2018.01)
*G06F 21/62* (2013.01)
*G16H 50/70* (2018.01)
*G06N 20/00* (2019.01)

(52) U.S. Cl.
CPC ......... *G16H 40/20* (2018.01); *G06F 21/6254* (2013.01); *G06N 20/00* (2019.01); *G16H 50/70* (2018.01)

(58) Field of Classification Search
None
See application file for complete search history.

(56) References Cited

U.S. PATENT DOCUMENTS

| | | | | |
|---|---|---|---|---|
| 2007/0204066 A1* | 8/2007 | Cohen | ................... | G16H 10/60 709/246 |
| 2009/0287837 A1* | 11/2009 | Felsher | ................. | G06F 19/328 709/229 |
| 2013/0159021 A1* | 6/2013 | Felsher | ................. | G06F 19/328 705/3 |
| 2014/0052475 A1* | 2/2014 | Madan | ................ | G06F 19/3418 705/3 |
| 2014/0081669 A1* | 3/2014 | Raduchel | .......... | H04W 12/0609 705/3 |
| 2014/0357961 A1* | 12/2014 | Meltzer | ................ | A61B 5/0002 600/301 |
| 2015/0007249 A1* | 1/2015 | Bezzi | .................. | G06F 21/6254 726/1 |

(Continued)

*Primary Examiner* — Michael Tomaszewski
*Assistant Examiner* — Jay M. Patel
(74) *Attorney, Agent, or Firm* — Fish & Richardson P.C.

(57) ABSTRACT

A computer-assisted method to timely provide notifications of treatments, the method including receiving de-identified longitudinal medical records, receiving notification data, identifying anonymized patients that received the treatment, identifying notifications for the treatment that were received by the recipients, determining, for each of the identified notifications, whether the recipient is an anonymized patient identified as having received the treatment, determining, for each of the identified notifications for the treatment determined to be received by a recipient that is an anonymized patient identified as having received the treatment, a time relationship between the time when the treatment was received by the anonymized patient and the time that the notification was received by the recipient that is the anonymized patient, and determining, for each of the anonymized patients that received the treatment, associations between one or more time relationships for notifications received by the anonymized patient.

18 Claims, 11 Drawing Sheets

(56) References Cited

U.S. PATENT DOCUMENTS

| | | | |
|---|---|---|---|
| 2015/0046192 A1* | 2/2015 | Raduchel | G16H 10/65 705/3 |
| 2015/0134346 A1* | 5/2015 | Hyde | G06F 19/3462 705/2 |
| 2015/0244687 A1* | 8/2015 | Perez | G16H 10/60 726/4 |
| 2015/0269355 A1* | 9/2015 | Tidor | G16H 10/20 705/3 |
| 2017/0161439 A1* | 6/2017 | Raduchel | G06Q 10/063 |

* cited by examiner

FIG. 8

Digital Campaign Optimization - Output

Back to Input Page

900

Summary

| | Actual through Date | Current Forecast for Full Campaign | Proposed Forecast for Full Campaign | Gains |
|---|---|---|---|---|
| Impression Allocation for Full Campaign | 24,952,587 | 100,000,000 | 137,311,349 | |
| Total Budget $ | $ 341,721 | $ 1,520,800 | $ 1,520,800 | |
| Average CPM | $ 13.69 | $ 15.21 | $ 11.08 | |
| NTB Impact Rate | 0.105% | 0.042% | 0.042% | |
| Projected NTB Estimated # of Patients | 7,867 | 13,109 | 14,424 | 1,315 |
| % Change from Pre-Optimization | | | | 10% |

Proposed Allocation

| Channel | Site | Placement | Total Impressions Served to Date | Current Remaining Allocation for Full Campaign | Proposed Remaining Allocation for Full Campaign |
|---|---|---|---|---|---|
| display | publisher A | placement 1234 | 3,744,213 | 16,255,787 | 4,570,885 |
| display | publisher B | placement 2345 | 3,408,447 | 11,591,553 | 5,962,428 |
| display | publisher C | placement 3456 | 807,000 | 4,993,000 | 27,469,886 |
| display | publisher D | placement 4567 | 2,345,880 | 7,654,120 | 2,666,861 |
| display | publisher D | mobile placement 9876 | 23,273 | 176,727 | 1,276,036 |
| display | publisher E | placement 5678 | 3,575,727 | 1,424,273 | 19,433,776 |
| display | publisher E | placement 6789 | 2,690,880 | 17,309,120 | 4,696,426 |
| display | publisher E | placement 7890 | 1,473,373 | 2,526,627 | 3,293,865 |
| display | publisher E | placement 7890 section A | 234,027 | 765,973 | 1,237,469 |
| display | publisher E | placement 7890 section B | 915,487 | 4,084,513 | 1,909,510 |
| display | publisher E | placement XYZ | 2,405,120 | 7,594,880 | 2,688,708 |
| display | publisher E | placement 8901 section A | 1,840,580 | 159,420 | 18,540,118 |
| display | publisher E | placement 8901 section B | 1,488,580 | 511,420 | 18,618,995 |
| Total | | | 24,952,587 | 75,047,413 | 112,358,762 |

SYSTEM AND METHOD FOR TIMELY NOTIFICATION OF TREATMENT

BACKGROUND

Medical patients may receive various treatments. For example, a medical patient may be prescribed medication by a healthcare professional.

OVERVIEW

In one aspect, some implementations provide a computer-implemented method that includes: receiving, from one or more database systems each comprising non-volatile data storage devices, de-identified longitudinal medical records, each de-identified longitudinal medical record representing a record of a different anonymized patient and encoding information identifying a treatment received by the anonymized patient, information identifying a time the treatment was received, and an identifier that uniquely distinguishes the anonymized patient from other anonymized patients, the records devoid of information identifying the patients; receiving, from one or more database systems each comprising non-volatile data storage devices, notification data including notification records, each notification record encoding information identifying a type of notification provided, information identifying a time the notification was received, and information referring to a recipient that received the notification; identifying, from the de-identified longitudinal medical records, anonymized patients that received the treatment; identifying, from the notification data, notifications for the treatment that were received by the recipients; determining, for each of the identified notifications that were received by the recipients, whether the recipient is an anonymized patient identified as having received the treatment; determining, for each of the identified notifications for the treatment determined to be received by a recipient that is an anonymized patient identified as having received the treatment, a time relationship between the time when the treatment was received by the anonymized patient and the time that the notification was received by the recipient that is the anonymized patient; determining, for each of the anonymized patients that received the treatment, associations between one or more time relationships for notifications received by the anonymized patient; and generating, using machine learning, an impact model representing an impact of a notification on a treatment being received based on the determined associations between the time relationships.

Implementations may include one or more of the following features. Determining, for each of the identified notifications that were received by the recipients, whether the recipient is an anonymized patient identified as having received the treatment may include determining that the information referring to a recipient that received the notification and the identifier that uniquely distinguishes the anonymized patient from other anonymized patients both refer to the same person. Determining, for each of the identified notifications for the treatment determined to be received by a recipient that is an anonymized patient identified as having received the treatment, a time relationship between the time when the treatment was received by the anonymized patient and the time that the notification was received by the recipient that is the anonymized patient may include determining a time when a treatment was received by a particular anonymized patient, determining a time when a notification for the treatment was received by a particular recipient corresponding to the particular anonymized patient, and determining a time relationship that represents a time length between the time when the treatment was received by the particular anonymized patient and the time when the notification for the treatment was received by the particular recipient corresponding to the particular anonymized patient. Determining, for each of the anonymized patients that received the treatment, associations between one or more time relationships for notifications received by the patient may include determining for a particular patient that a first notification for the treatment was received by the particular patient and a second notification for the treatment was received by the particular patient. Generating, using machine learning, an impact model representing an impact of a notification on a treatment being received based on the determined associations between the time relationships may include generating the impact model using a random survival forest analysis with the determined associations between the time relationships. The impact model may represent an impact of a notification on a treatment being received exponentially decayed from time when the notification was initially provided to a patient to a time the treatment was received by the patient.

The method may further include determining, for each of the notifications, an impact of the notification on a treatment being received based on the impact model and the determined time relationships, determining a forecast model based on the impacts determined for the notifications, where the forecast model stores, for each type of notification, a notification type label that is indicative of a relationship between a number of patients receiving a treatment and a number of recipients receiving notifications for the treatment and scheduling notifications based on the forecast model. Implementations may include one or more of the following features. Determining, for each of the notifications, an impact of the notification on a treatment being received based on the impact model and the determined time relationships may include determining an impact for a first notification to a recipient through a first type of notification based on a time relationship for the first notification and determining an impact for a second notification to the recipient through a second type of notification based on a time relationship for the second notification. Determining, for each of the notifications, an impact of the notification on a treatment being received based on the impact model and the determined time relationships may include aggregating impacts of a particular type of notification on a treatment being received over all the patients and time. Determining a forecast model based on the impacts determined for the notifications, where the forecast model stores, for each type of notification, a notification type label that is indicative of a relationship between a number of a patients receiving a treatment and a number of recipients receiving notifications for the treatment may include determining, for each type of notification, a curve fitting a number of patients that previously received the treatment with a number of notifications previously provided to notification recipients. Determining a forecast model based on the impacts determined for the notifications, where the forecast model stores, for each type of notification, a notification type label that is indicative of a relationship between a number of a patients receiving a treatment and a number of recipients receiving notifications for the treatment may include determining the forecast model as a sigmoid function considering the diminishing effect of number of notifications received by recipients on number of patients that receive a treatment. Determining a forecast model based on the impacts determined for the notifications, where the forecast model stores, for each type of notification, a notification type label that is indicative of a relationship between a number of a patients receiving a treatment and a number of recipients receiving notifications for the treatment may include determining an initial forecast model for model patients based on the impacts determined for the notifications and projecting the initial forecast model to potential patients.

Implementations may include one or more of the following features. Scheduling notifications based on the forecast model may include determining a notification plan for timely notifying potential patients of treatments based on the forecast model. Determining a notification plan for timely notifying potential patients of treatments based on the forecast model may include receiving notification constraints for the plan, determining that increasing a number of notifications for a particular channel increases a number of treatments received according to the forecast model and satisfies the notification constraints, and determining a total number of notifications of each type that increases total forecasted number of received treatments. Scheduling notifications based on the forecast model may include providing notifications for the treatment to recipients. An anonymized patient may be a patient for which the patient's identity cannot be determined but is distinguishable from other anonymized patients.

In another aspect, some implementations provide a computer system comprising one or more processors, configured to perform the operations of: receiving, from one or more database systems each comprising non-volatile data storage devices, de-identified longitudinal medical records, each de-identified longitudinal medical record representing a record of a different anonymized patient and encoding information identifying a treatment received by the anonymized patient, information identifying a time the treatment was received, and an identifier that uniquely distinguishes the anonymized patient from other anonymized patients, the records devoid of information identifying the patients; receiving, from one or more database systems each comprising non-volatile data storage devices, notification data including notification records, each notification record encoding information identifying a type of notification provided, information identifying a time the notification was received, and information referring to a recipient that received the notification; identifying, from the de-identified longitudinal medical records, anonymized patients that received the treatment; identifying, from the notification data, notifications for the treatment that were received by the recipients; determining, for each of the identified notifications that were received by the recipients, whether the recipient is an anonymized patient identified as having received the treatment; determining, for each of the identified notifications for the treatment determined to be received by a recipient that is an anonymized patient identified as having received the treatment, a time relationship between the time when the treatment was received by the anonymized patient and the time that the notification was received by the recipient that is the anonymized patient; determining, for each of the anonymized patients that received the treatment, associations between one or more time relationships for notifications received by the anonymized patient; and generating, using machine learning, an impact model representing an impact of a notification on a treatment being received based on the determined associations between the time relationships.

In yet another aspect, some implementations provide a computer-readable medium, comprising software instructions, which when executed by a processor of a computer, causes the computer to perform the operations of: receiving, from one or more database systems each comprising non-volatile data storage devices, de-identified longitudinal medical records, each de-identified longitudinal medical record representing a record of a different anonymized patient and encoding information identifying a treatment received by the anonymized patient, information identifying a time the treatment was received, and an identifier that uniquely distinguishes the anonymized patient from other anonymized patients, the records devoid of information identifying the patients; receiving, from one or more database systems each comprising non-volatile data storage devices, notification data including notification records, each notification record encoding information identifying a type of notification provided, information identifying a time the notification was received, and information referring to a recipient that received the notification; identifying, from the de-identified longitudinal medical records, anonymized patients that received the treatment; identifying, from the notification data, notifications for the treatment that were received by the recipients; determining, for each of the identified notifications that were received by the recipients, whether the recipient is an anonymized patient identified as having received the treatment; determining, for each of the identified notifications for the treatment determined to be received by a recipient that is an anonymized patient identified as having received the treatment, a time relationship between the time when the treatment was received by the anonymized patient and the time that the notification was received by the recipient that is the anonymized patient; determining, for each of the anonymized patients that received the treatment, associations between one or more time relationships for notifications received by the anonymized patient; and generating, using machine learning, an impact model representing an impact of a notification on a treatment being received based on the determined associations between the time relationships.

The details of one or more aspects of the subject matter described in this specification are set forth in the accompanying drawings and the description below. Other features, aspects, and advantages of the subject matter will become apparent from the description, the drawings, and the claims.

DESCRIPTION OF DRAWINGS

FIG. 8 illustrates an example user interface for receiving notification constraints for determining a plan for timely providing notifications.

FIGS. 9 and 10 illustrate example plans for timely providing notifications.

Like reference symbols in the various drawings indicate like elements.

DETAILED DESCRIPTION

Figure 1A:
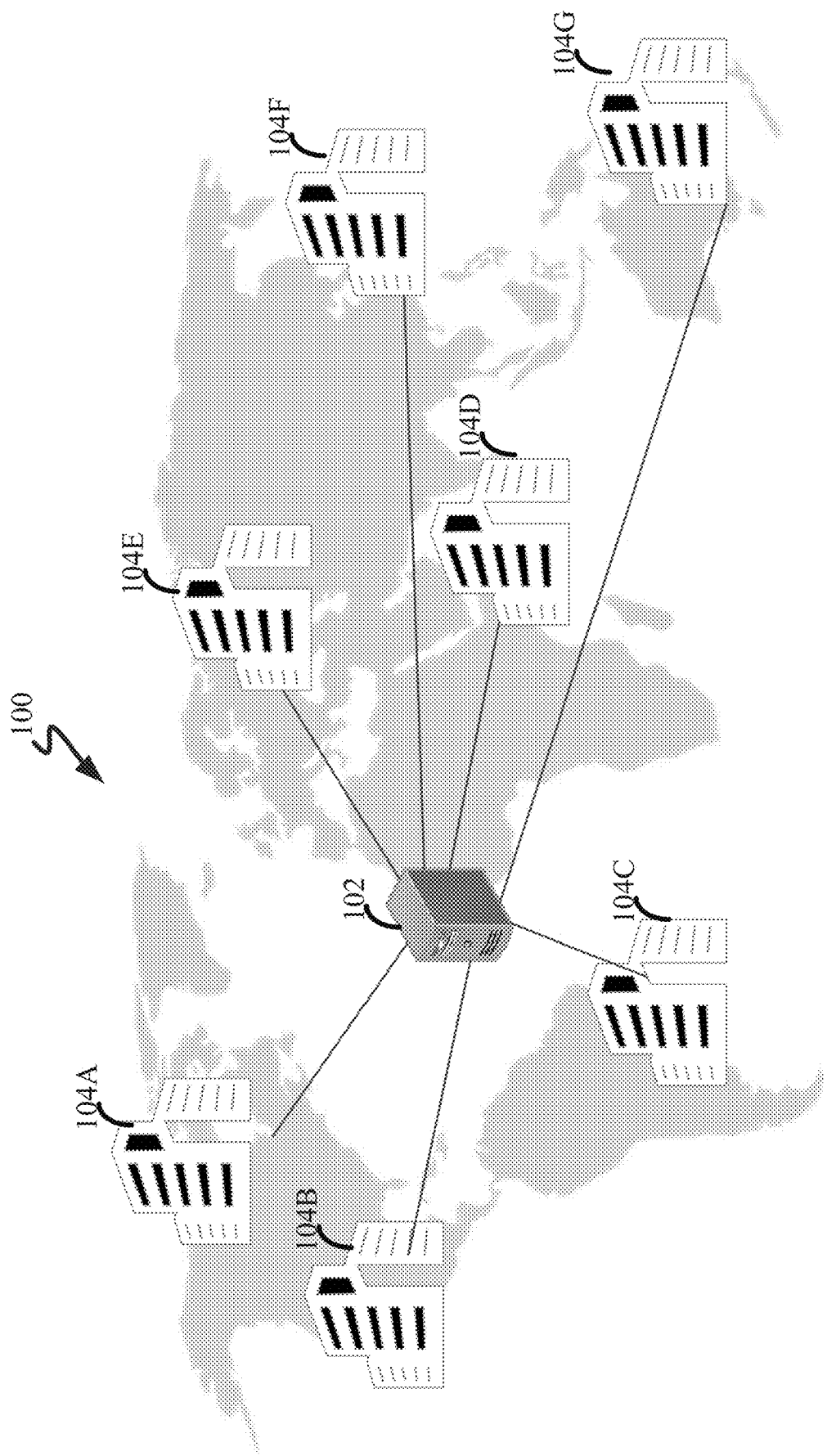
FIG. 1A illustrates an example of a system for deriving de-identified longitudinal medical data from various data supplier sites.

Reconciling disparate records from across different databases can be computationally burdensome to the extent that many desirable database operations are precluded across large and complex databases. For example, in the health care field, a variety of epidemiological studies would reveal links between disparate events. These problems are particularly acute in that the underlying databases may be de-identified in order to satisfy medical privacy concerns. Further, the size of the databases, which can include complex coding for complex and disparate diagnoses may make establishing links between different events even more computationally intensive as a specified item may be compared against countless other items, diagnoses, stimuli, and conditions. These operations are further complicated by different data sources that are formatted in different conventions and with varying degrees of completeness. Further, databases may be constantly updated with large volumes of new information. Thus, newly-received records must be reconciled with and compared to existing records and databases in order to ascertain new trends and real-time information.

The problem is particularly acute where longitudinal data associated with a de-identified label is reconciled between two different data sources with two different time sequences that describe different and sometimes unrelated activity. In order to perform the requisite correlation between the two different data sources, the data must be formatted in a manner that facilitates ready comparison of two different data points from each of the data sources. Once rapid comparison of disparate sources can be relied upon, an organization, such as a Patient Safety Organization (PSO) can act in reliance upon the identified correlations and work to address the correlations and derived identifications. For example, one such correlation may be associated with a breach in the desired activity (e.g., a standard of care). A medical administrator then may work to identify these deviations as fault or alarm conditions and take corrective action in real-time. Note that the deviations need not formally be relative to some regulatory standard (e.g., the standard of care). Instead, the deviation may exist relative to desired behavior (e.g., an internal hospital policy).

Based on the architecture and organization described above, a variety of configurations may be used to facilitate analysis of patent records organized longitudinally according to a first timeline relative to another source of data organized according to a second timeline. In one configuration, this disclosure generally describes a system and a method for timely providing notifications of treatments to a patient population, and the reaction to notifications. There may be significant problems in determining an impact of a notification about a treatment provided to a patient on a receipt of the treatment by the patient as, in healthcare, treatments generally do not immediately follow notifications of treatments. For example, a patient may not get a prescription without a doctor, the doctor may recommend other lifestyle changes, other treatments, order tests, etc. before prescribing the patient a drug, the patient then may need to go to the pharmacy to get the prescribed drug. Additionally, the patient may need to have insurance or some other way to supplement the expense of the prescribed drug before making the purchase. Additionally, in healthcare, patient information generally must be anonymized. As described in this description, treatment may refer to medical events such as seeing a doctor, receiving a prescription, receiving prescribed drugs from a pharmacy or undergoing an operation.

Accordingly, in some implementations, de-identified longitudinal medical records may be collected from data servers at medical service providers that record filled prescription information, medical operations, doctor visits, or other medical events for patients. The information may generally include records of different anonymized patients, where each record identifies one or more treatments received by the anonymized patient, the one or more times the treatments were received by the anonymized patient, and an identifier that uniquely distinguishes the anonymized patient from other anonymized patients. The identifier may refer to a de-identified patient, which may also be referred to as an anonymized patient. The de-identification means no identity information, such as name, address, birth date, or social security information, is available in the recorded information. Instead, each patient is referenced by an anonymous tag that is specific to the patient. Accordingly, an anonymized patient may be a patient for which the patient's identity cannot be determined but is distinguishable from other anonymized patients. Generally, the anonymous tag is doubly encrypted using a key specific to a data supplier (such as a data server at a pharmacy) and another key specific to a longitudinal database.

Additionally, notification data may be collected from data servers of notification providers that record notifications provided to recipients. A notification may include text, one or more images, one or more videos, or one or more audio identifying a treatment. The notifications may be placed in various locations, e.g., on websites or in mobile applications. For example, a first type of notification may be provided with an image on a first website, and a second type of notification may be provided with text on a second website. The notification data may include notification records that each identify a type of notification provided, a time the notification was received, and the recipient of the notification. Interestingly, relationships between the patients of the medical data and recipients of the notification data may be identified and time relationships between when patients received a treatment and when the patients received a notification regarding the treatment may be determined. The time relationships may then be used to determine impacts of the notifications on the patients receiving the treatment. The impacts of the notifications may be used to forecast a future effect of various types of notification, and a plan for providing notifications in the feature may be determined based on the forecast.

FIG. 1A illustrates an example system 100 for obtaining de-identified longitudinal medical records. The medical records may include treatment data in the form of prescription data. The prescription may include a pharmaceutical product such as a prescription drug approved by a regulatory agency, such as the Federal Drug Administration (FDA), the European Medicines Agency (EMA), the Medicines and Healthcare products Regulatory Agency (MHRA). The pharmaceutical product can also include approved medical devices. The prescriptions may be filled at multiple sites, such as pharmacies 104A to 104G. These sites can cover a geographic region, for example, a region in a particular country. These sites may also be located globally, for example, the North American continent, or the European Union.

Prescription data for each participant patient may be collected from each pharmacy store. In one example, a pharmacy database may collect prescription data from all pharmacy stores on a daily basis. The pharmacy database includes non-volatile data storage devices. Each pharmacy store may house its own data server in communication with the pharmacy database to transfer prescription data on a daily basis. The prescription data records the information about a particular prescription when the prescription was filled. As disclosed herein, the prescription data for each participant patient, as recorded at the pharmacy store at the time of filling, is de-identified such that the data does not include information capable of identifying the particular participant patient. Examples of such identifying information include: patient's name, patient's insurance identification number, patient's Medicare/Medicaid identification number, patient's social security number, patient driver's license number, etc. In some implementations, such identifying information may be converted by a one-way hash-function to generate an alpha-numerical string. The alpha-numerical string conceals the identity of the individual participant patient, thereby maintaining confidentiality of the data as the data is being reported, for example, daily from the sites 104A to 104G to the central server 102. There, data corresponding to the same participant patient may be linked by virtue of the matching alpha-numerical string. Thus, data for the same participant patient may be longitudinally tracked for each individual, without compromising confidentiality of the individual patients, even though the patient can fill the prescription at various stores and the patient can receive a prescription for a healthcare product from various healthcare professionals.

Additionally or alternatively, the de-identified longitudinal medical records may include other forms of data. For example, the de-identified longitudinal medical records may include data describing operations performed on a patient and when the operations were performed, when a patient made a visit to a particular doctor, when a doctor performed a diagnosis on a patient, and other events. In these instances, the sites may be medical service providers that include pharmacy stores and other types of medical service providers, e.g., doctor's offices or hospitals.

Figure 1B:
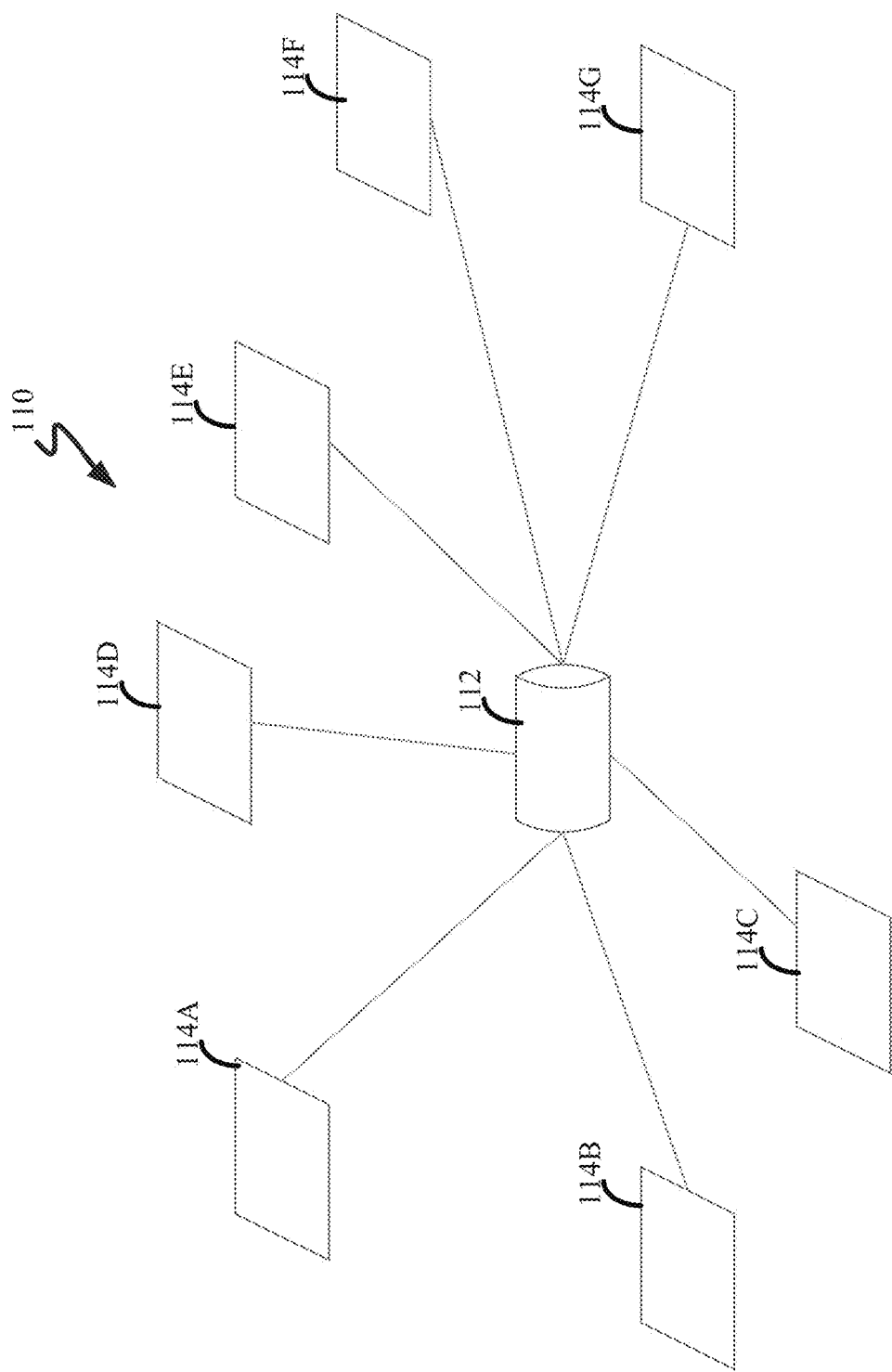
FIG. 1B illustrates an example of a system for aggregating medical data from data servers at medical service providers longitudinally tracking the treatment pattern of human patients.

FIG. 1B illustrates an example work flow 110 for collecting data of patient recipients from data servers at various medical service providers and longitudinally tracking the medical record of each individual patient recipient over time. Data 114A-114G may correspond to prescription data reported from each pharmacy store. In some implementations, data 114-114G may be reported from data servers at each pharmacy store on a daily basis, for example, at the end of business data local time. Data 114A-114G remain de-identified to preserve confidentiality, as disclosed herein. In this illustrated work flow, each pharmacy store may employ the same one-way hashing function to anonymize data records of each patient. As a result, reported prescription data 114A-114G, as received at central server 102 to update database 112, include the same de-anonymized key for prescription records from the same patient, even if the patient may move to another pharmacy store, another healthcare professional, or another healthcare provider (e.g., health insurance carrier, pharmacy insurance carrier). The central server 102 may match prescription data records from the same patient recipient to update database 112, which contains data records reported earlier for the same patient recipient.

In some implementations, however, the de-identified data may be further encrypted before the data is reported to central server 102 to update database 112. For illustration, data 114A-114G may be encrypted using a symmetric encryption key specific to each pharmacy store. The symmetric encryption key may only be known to the pharmacy store and central server 102. Thus, only the participant site can encrypt the de-identified data with the symmetric key and only the central server 102 can decrypt the encrypted de-identified data with the particular symmetric key. In another illustration, a public-key infrastructure (PKI) may be used such that the reported data may be encrypted with the public key of the central server 102 so that only the central server 102 can decrypt using its private key. In other illustrations, the central server 102 and pharmacies 104A-104G may exchange messages using the PKI to establish an agreed-on symmetric key.

As discussed above, the data 114A-114G may correspond to other data besides prescription data. For example, the data 114A-114G may describe operations performed on a patient and when the operations were performed, when a patient made a visit to a particular doctor, when a doctor performed a diagnosis on a patient, and other events received from medical service providers that include pharmacy stores and other types of medical service providers, e.g., doctor's offices or hospitals.

Figure 1C:
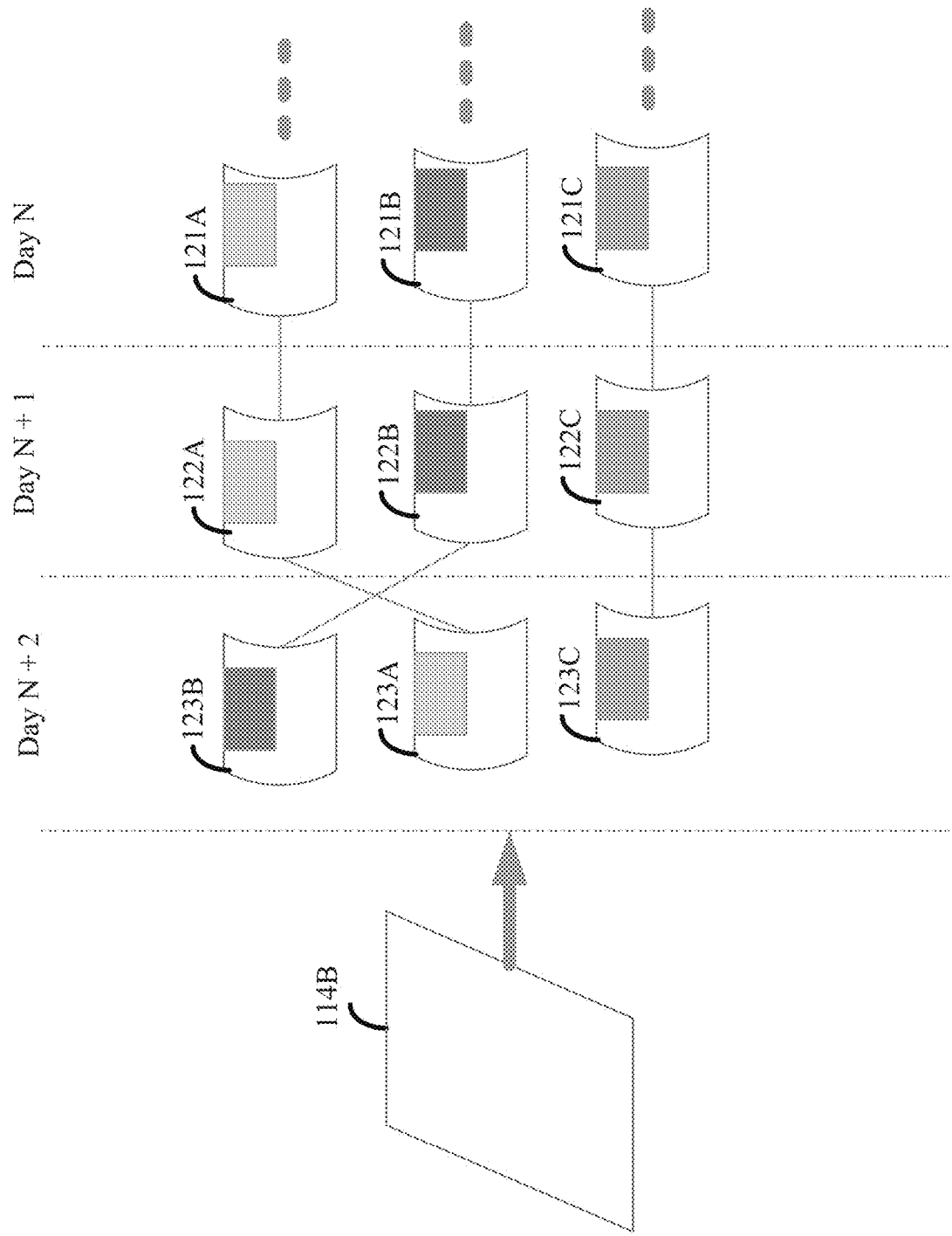
FIG. 1C illustrates an example of linking medical data of the patients.

FIG. 1C illustrates an example linkage of daily reported medical data for the patient recipients based on matching anonymized tags. As illustrated, the daily received prescription data (for example, data 114B from pharmacy 104B) correspond to patient recipients. The de-identification process allows such prescription data to remain anonymous. In some implementations, the de-identified data from the same patient may be linked at central server 102. As illustrated, data are received on different days for the patient recipients. For example, on time point N, de-identified prescription data 121A to 121C may be received. Likewise, on time point N+1, de-identified prescription data 122A to 122C are received. Similarly, on time point N+2, de-identified data 123A to 123C may be received. These de-identified prescription data correspond to different patient recipients. Based on matching tags, such as matching de-identified alpha-numerical strings, the de-identified prescription data from each patient recipient may be linked and hence the prescription activity of a particular patient recipient can be longitudinally tracked. In some implementations, the matching tags may include graphic representations as well as alpha-numerical strings. The graphic representations are also de-identified to remove personally identifiable information of the participant patient. In some instances, the alpha-numerical strings or graphical representations may be tags to the actual prescription data record, which may be referred to as part of the metadata. In other instances, the alpha-numerical strings or graphical representations may be embedded to the actual prescription data record itself. In still other instances, the alpha-numerical strings or graphical representations may be part of the metadata and embedded in the actual prescription data record. The implementations of both the tag and the embedding may further deter alterations or modifications of the data records being reported from each participant site. When the received daily data records are linked with earlier data records of the same patient recipients, database 112 may be updated. The updated database may allow a variety of data analytics to be generated, revealing the interesting insights of prescription usage pattern for each patient recipient as well as the statistical prescription pattern of each healthcare professional, as discussed below.

As discussed above, the de-identified prescription data 121A to 121C may correspond to other de-identified data besides prescription data. For example, the de-identified data may describe operations performed on a patient and when the operations were performed, when a patient made a visit to a particular doctor, when a doctor performed a diagnosis on a patient, and other events.

Figure 2:
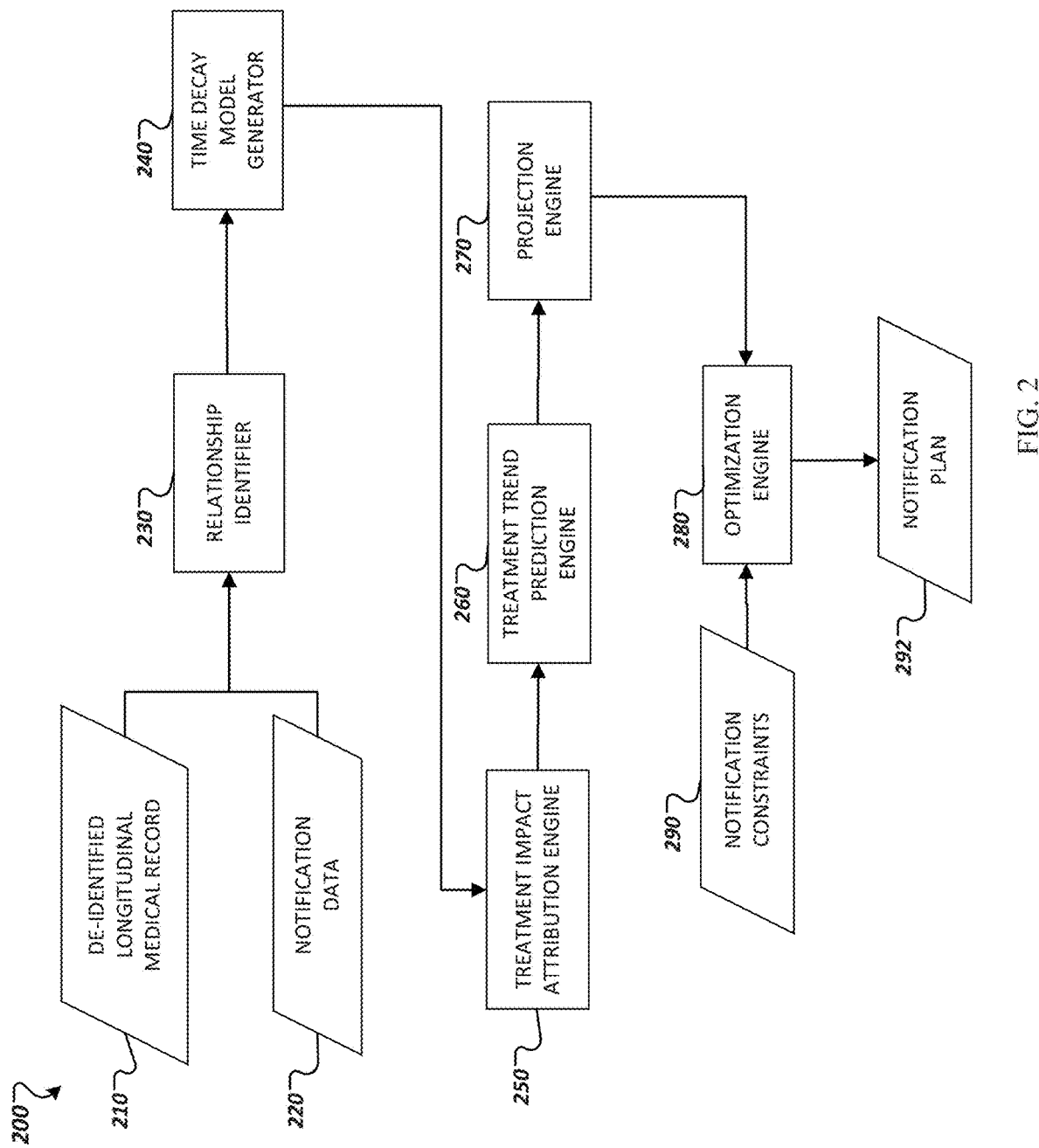
FIG. 2 illustrates an example of a block diagram of a system for providing timely notification of treatments.

FIG. 2 illustrates an example of a block diagram of a system 200 for providing timely notification of treatments. The system 200 may include a relationship identifier 230 that identifies relationships between de-identified longitudinal medical records and notification data, a time decay model generator 240 that determines an impact model based on the relationships, a treatment impact attribution engine 250 that determines an impact of notifications on a treatment being received, a treatment trend prediction engine 260 that determines an initial forecast for the anonymized patients based on the determined impacts, a projection engine 270 that determines a projected forecast for potential patients from the initial forecast, and an optimization engine 280 that determines a notification plan based on the projected forecast.

In more detail, the relationship identifier 230 may identify relationships between patients anonymously identified by the de-identified longitudinal medical records 210 and recipients of identified by the notification data 220. As described above, the de-identified longitudinal medical records 210 may be collected from data servers at medical service providers that record filled prescription information, medical operations, doctor visits, or other medical events for patients. The information may generally include records of different anonymized patients, where each record identifies one or more treatments received by the anonymized patient, the one or more times the treatments were received by the anonymized patient, and an identifier that uniquely distinguishes the anonymized patient from other anonymized patients. The notification data 220 may be collected from data servers of notification providers that record notifications provided to recipients. The notification data may include notification records that each identify a type of notification provided, a time the notification was received, and the recipient of the notification.

The relationship identifier 230 may obtain the de-identified longitudinal medical records 210 and the notification data 220, and identify relationships between anonymized patients and recipients based on identifying, from the de-identified longitudinal medical records, anonymized patients that received the treatment, identifying, from the notification data, notifications for the treatment that were received by the recipients, and determining, for each of the identified notifications that were received by the recipients, whether the recipient is an anonymized patient identified as having received the treatment. For example, the relationship identifier 230 may identify from a medical record that an anonymized patient identified as "ad978zfvd3426oiu90" received a particular treatment, identify from the notification data that a recipient identified as "ad978zfvd3426oiu90" received a notification for the particular treatment, and that the identifiers both have the value "ad978zfvd3426oiu90." In some implementations, the relationship identifier 230 may, one or more of, determine whether notification records are for notifications for other treatments and determine to ignore those notifications or determine whether treatments indicated by the medical records are for other treatments and determine to ignore those indications in the medical records. Additionally or alternatively, the relationship identifier 230 may determine that the identifiers match. For example, the relationship identifier 230 may determine that the identifier of an anonymized patient in a medical record indicates demographics of the anonymized patient, that are insufficiently detailed to identify the anonymized patient, match demographics indicated by the identifier of a recipient in a notification record.

The time decay model generator 240 may determine an impact model based on the relationships determined by the relationship identifier 230. The impact model may represent an impact of a notification on a treatment being received based on a time relationship between when a treatment was received by a patient and a notification was received by a recipient corresponding to the patient. For example, the time decay model generator 240 may determine an impact model that models an impact of 66% for a notification received fifteen days before a treatment is received and an impact of 33% for a notification received thirty days before a treatment is received. In some implementations, the impact model may include a model that is exponentially decayed from time when the notification was initially provided to a patient to a time the treatment was received by the patient. For example, the time decay model generator 240 may determine coefficients for an exponential function that receives as an input a time relationship and outputs an impact. In some implementations, the impact model may be specific to notification type. For example, the time decay model generator 240 may generate an impact model that provides different impacts for the same time relationship for notifications of different types. In some other implementations, the impact model may not be specific to notification type. For example, the time decay model generator 240 may generate an impact model that provides the same impact for the same time relationship for notifications of the same type.

The time decay model generator 240 may determine the impact model based on determining time relationships between times when treatments were received by anonymized patients and times when notifications were received by recipients corresponding to the anonymized patients, determining associations between one or more time relationships for notifications received by the anonymized patients, and determining the impact model from the determined associations between the time relationships. For example, the time decay model generator 240 may determine from the medical records 210 that anonymized patient "ad978zfvd3426oiu90" fulfilled a prescription for "Drug X" on Jul. 23, 2015, from the notification data 220 that a recipient determined to correspond to anonymized patient "ad978zfvd3426oiu90" received a notification regarding "Drug X" on Jul. 8, 2015, and as result, determine a time relationship of fifteen days, determine from the notification data 220 that a recipient determined to correspond to anonymized patient "ad978zfvd3426oiu90" received a notification regarding "Drug X" on Jun. 23, 2015, and as result, determine a time relationship of thirty days, determine that both notifications were received by anonymized patient "ad978zfvd3426oiu90," and in response, determine that the time relationship of thirty days and fifteen days for anonymized patient "ad978zfvd3426oiu90" are both associated with anonymized patient "ad978zfvd3426oiu90" receiving the treatment. In another example, the time decay model generator 240 may determine from the medical records 210 that anonymized patient "oinj32o908twvc2" fulfilled a prescription for "Drug X" on Jul. 1, 2015 and from the notification data 220 and determined relationships that a recipient corresponding to anonymized patient "oinj32o908twvc2" received a notification regarding "Drug X" on Jun. 1, 2015, and as result, determine a time relationship of thirty days.

From the associations between time relationships, the time decay model generator 240 may determine the impact model. For example, the time decay model generator 240 may use machine-learning, e.g., Least Absolute Shrinkage and Selection Operator (LASSO), Cox Proportional Hazard (CPH) model, ensemble learning by random survival forest (RSF), with the de-identified longitudinal medical records 210, the notification data 220, and the determined time relationships to determine coefficients of an exponential function. The time decay model generator 240 may use random survival forest by randomly under sampling patients indicated by the medical records 210 that were not treated with the particular treatment, combine the under sampled data with the data of anonymized patients indicated by the medical records 210 that were treated with the particular treatment, apply random survival forest to derive an impact of a notification each day to the treatment being received, e.g., scores of impact of a notification each day to treatment being received may be generated, repeating these steps, e.g., for 50,000, 100,000 or some other number of times, and average the impacts, and then fitting a curve to impact decay over time based on the averaged impacts.

The treatment impact attribution engine 250 may determine an impact of notifications on a treatment being received based on the impact model determined by the time decay model generator 240. In particular, the treatment impact attribution engine 250 may attribute an impact of different types of notifications indicated by the notification data 220 over all anonymized patients identified by the medical records 210 and time based on the impact model. For example for each type of notification, the treatment impact attribution engine 250 may sum an impact of the type of notification on each anonymized patient indicated by the medical records 210 receiving the treatment based on the impact model. From the attribution, the treatment impact attribution engine 250 may determine different impacts of different types of notifications. For example, the treatment impact attribution engine 250 may determine that a particular type of notification has twice as much impact as another type of notification, i.e., results in twice as many patients receiving a treatment.

The treatment trend prediction engine 260 may determine an initial forecast model based on the impacts determined by the treatment impact attribution engine. For example, the treatment trend prediction engine 260 may determine an initial forecast model that models a number of patients identified in the medical records 210 that would receive a treatment based on a number of each type of notification provided. A forecast model may store, for each type of notification, a notification type label that is indicative of a relationship between a number of patients receiving a treatment and a number of recipients receiving notifications for the treatment. For example, a first notification type label for a first type of notification may reflect how a number of patients estimated to receive a treatment increases as a number of recipients of a notification of the first type of notification for that treatment increases and a second notification type label for a second type of notification may reflect how a number of patients estimated to receive a treatment increases as a number of recipients of a notification of the second type of notification for that treatment increases.

The treatment trend prediction engine 260 may determine the initial forecast model based on fitting the model to the number of treatments received indicated by the medical records 210 and the notifications provided indicated by the notification data 220. For example, the treatment trend prediction engine 260 may determine an initial forecast model that scales an impact of notifications of all types by an amount so that a number of patients forecasted to receive a treatment best matches the number of patients that actually received the treatment as indicated by the medical records 210 and the notification records 220. The treatment trend prediction engine 260 may determine the initial forecast model as a sigmoid function considering the diminishing effect of number of notifications received by recipients on number of patients that receive a treatment.

The treatment trend prediction engine 260 may generate more accurate initial forecast models as the amount of data increases across time. For example, at nine weeks data up to 100,000 notifications may be available, at thirteen weeks, data up to 150,000 notifications may be available, and at eighteen weeks data up to 200,000 notifications may be available, and the treatment trend prediction engine 260 may fit the initial forecast model to match the data.

The projection engine 270 may determine a projected forecast for potential patients from the initial forecast determined by the treatment trend prediction engine 260. For example, the projection engine 270 may project an initial forecast determined from a subset of patients with indicated by the medical records 210 to a set of all patients indicated by the medical records 210, then project from the set of all patients indicated by the medical records 210 to all recipients of notifications indicated by the notification data 220, and then project from all recipients of the notifications indicated by the notification data 220 to all potential recipients of the notification. The subset of patients of the initial forecast may be patients that have prescription drug activity within a predetermined number of months, e.g., the last three, six, twelve, or another number of months.

The projection engine 270 may project forecasts from a first group to a second group based on scaling on characteristics of the groups. For example, the projection engine 270 may determine that the initial forecast is prepared for a set of one hundred patients where 40% have high blood pressure, and that the medical records 210 for all one thousand patients have 20% with high blood pressure, and in response, modify the initial forecast by a factor of five.

The optimization engine 280 may determine a notification plan based on the projected forecast. For example, the optimization engine 280 may determine to provide one million of a particular type of notification and two million of another type of notification to increase a forecasted number of treatments. The optimization engine 280 may determine the notification plan based on notification constraints 290. The notification constraints 290 may include specifications of one or more of a budget, notification types available, notifications provided so far, notifications allocated, a minimum number of notifications for each type, a maximum number of notifications of each type, a remaining number of notifications to provide for each type, a cost for each type of notification, an available budget for each type of notification, or a total budget for a type of notification. For example, the notification constraints 290 may specify that a total of one million is available for notifications, three types of notifications are available, a first type of notification costs fourteen dollars per million provided, a second type of notification costs eighteen dollars per million provided, and a third type of notification costs sixteen dollars per million provided, and in response, based on the projected forecast model, the optimization engine 280 may determine to allocate two hundred thousand dollars to the first type of notification, five hundred thousand dollars to the second type of notification, and three hundred thousand dollars to the third type of notification.

The optimization engine 280 may receive the notification constraints from a user. For example, the optimization engine 280 may provide a graphical user interface for a user to input the notification constraints and change the notification constraints, and in response may update the notification plan and display the updated notification plan to the user through the graphical user interface.

In some implementations, the optimization engine 280 may receive indications of events and in response update a notification plan. For example, the optimization engine 280 may receive an indication that a flu epidemic is spreading, and in response, may determine to increase a number of allocations of a particular type of notification and decrease a number of allocations of another type of notification.

The optimization engine 280 may then schedule the notifications based on the forecast model. For example, the optimization engine 280 may cause the system 100 to provide notifications to recipients based on the notification plan. In another example, the optimization engine 280 may provide the notification plan to a notification provider for the notification provider to provide notifications in accordance with the notification plan.

Figure 3:
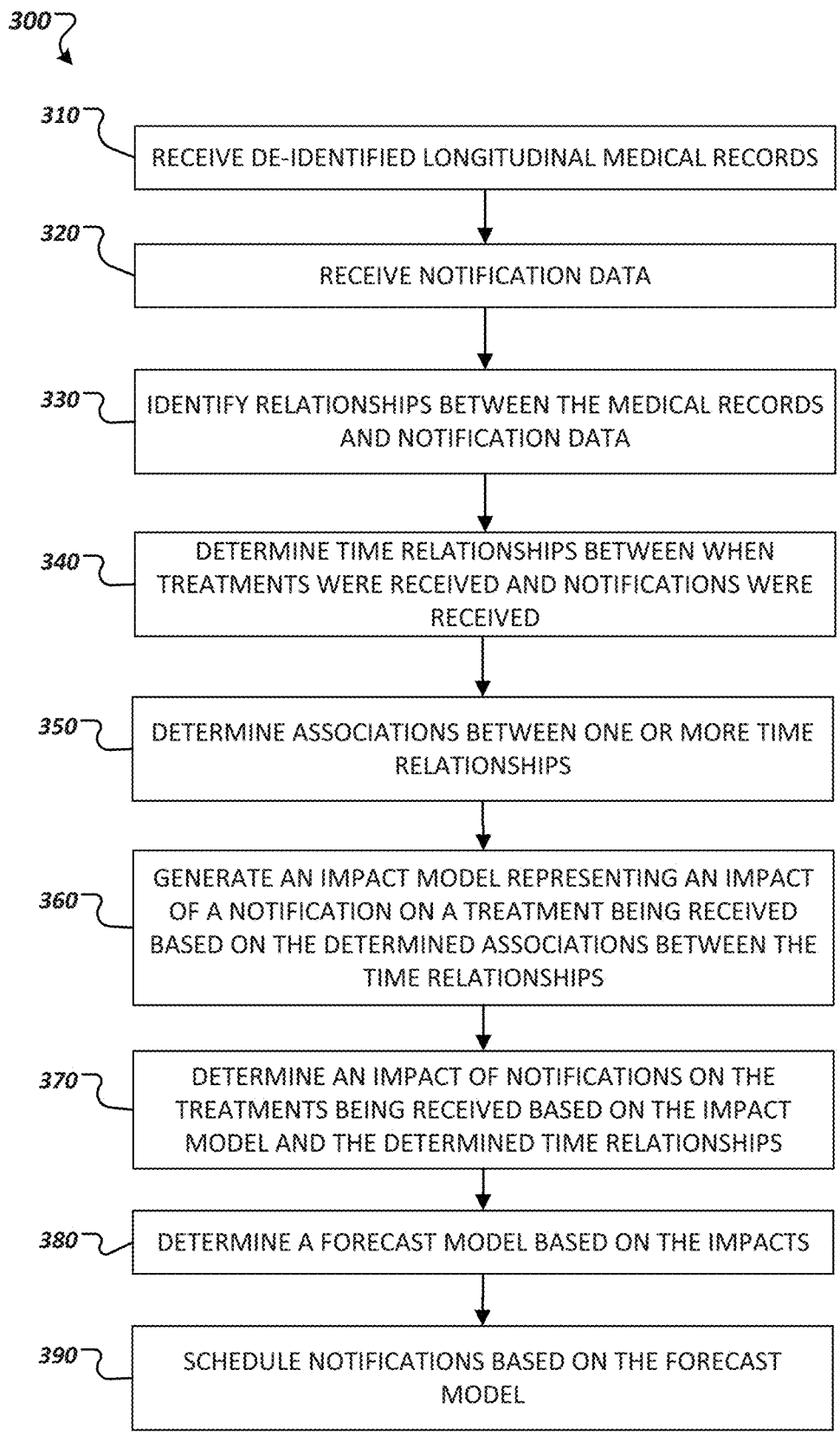
FIG. 3 illustrates an example of a flow chart for providing timely notifications of treatments.

FIG. 3 illustrates an example of a flow chart 300 for providing timely notifications of treatments. Initially, de-identified longitudinal medical records are received (310). For example, the relationship identifier 230 may receive de-identified longitudinal medical records from a database of a medical server provider. Before, after, or in parallel, notification data is received (320). For example, the relationship identifier 230 may receive notification data from a database of a notification provider.

Thereafter, relationships between the medical records and the notification data may be identified (330). For example, the relationships identifier 230 may determine that a particular medical record indicates that an anonymized patient received a particular treatment, determine that a particular notification record indicates that a recipient received a notification for the particular treatment, and determine that the particular medical record has an identifier, that refers to an anonymized patient, that is the same identifier representing a recipient that is associated with the particular notification record. Thereafter, time relationships between when treatments were received and notification were received may be determined (340). For example, the time decay model generator 240 may determine that sixty days based between when a recipient received a notification of a treatment and an anonymized patient corresponding to the recipient received the treatment. Next, associations between one or more time relationships may be determined (350). For example, the time decay model generator 240 may determine the time relationships that are notifications for treatments provided to the same recipient before the recipient received the treatment.

Next, an impact model representing an impact of a notification on a treatment being received based on the determined associations between the time relationships may be generated (360). For example, the time decay model generator 240 may generate the impact model that is exponentially decayed from time when the notification was initially provided to a patient to a time the treatment was received by the patient. Next, the impact of notifications on the treatments being received may be determined based on the impact model and the determined time relationships (370). For example, the treatment impact attribution engine 250 may determine the impact that a notification received sixty days before a treatment had on the treatment being received based on the impact model and that the notification was received sixty days before the treatment was received.

Thereafter, a forecast model may be determined based on the impacts (380). For example, the treatment trend prediction engine 260 may determine an initial forecast model for a set of patients based on the impacts and the projection engine 270 may project the initial forecast model to all potential notification recipients. Next, a plan for timely notifying may be determined based on the forecast model (390). For example, the optimization engine 280 may receive the forecast model and notification constraints specified by a user indicating types of notifications available and constraints on providing the notifications, and in response, determine a notification plan indicating how many of each type of notification should be provided.

Figure 4:
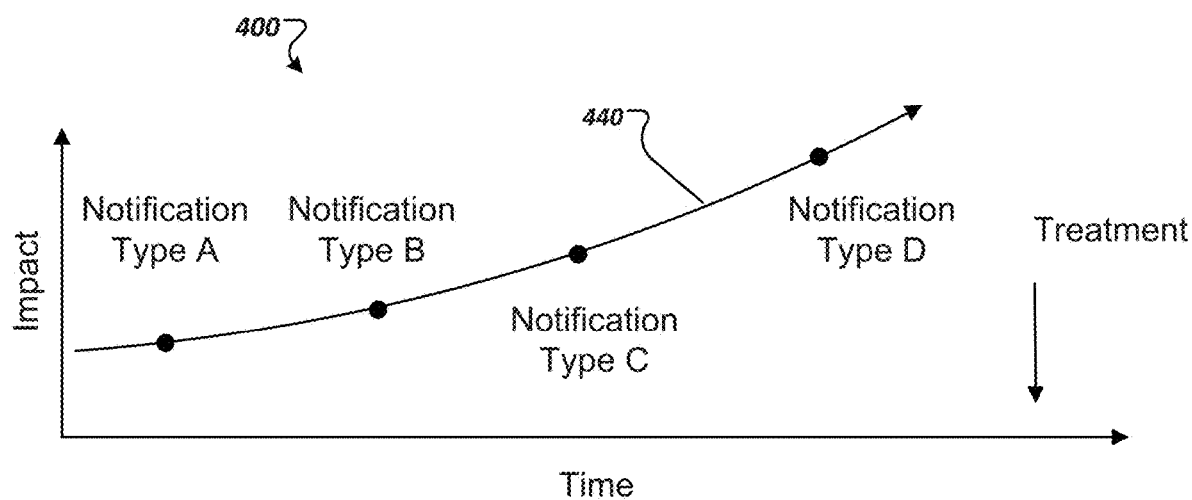
FIG. 4 illustrates an example timeline of notifications being provided and a treatment being received.

FIG. 4 illustrates an example timeline 400 of notifications being provided and a treatment being received. The timeline 400 may show time passing from left to right versus impact. The timeline 400 shows how as notifications are provided earlier from when a treatment is received, an impact of the notification decreases. For example, notification type A is provided most earliest from when a treatment is received and is associated with a lowest impact, notification type B is provided second most earliest from when a treatment is received and is associated with a second lowest impact, notification type C is provided third most earliest from when a treatment is received and is associated with a third lowest impact, and notification type D is provided least earliest from when a treatment is received and is associated with a highest impact.

Figure 5:
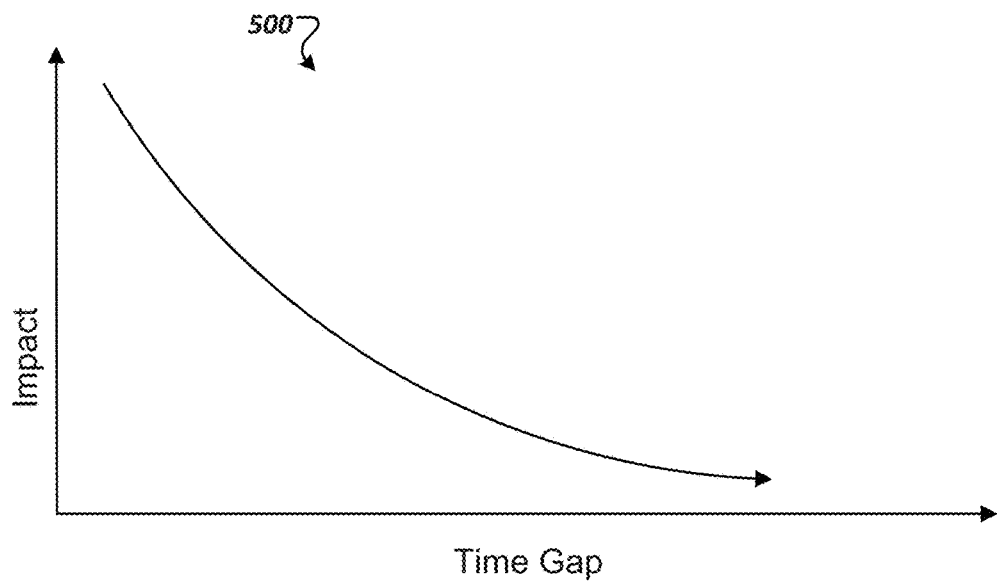
FIG. 5 illustrates an example graph of an impact of a notification with a time relationship between a notification and treatment.

FIG. 5 illustrates an example graph 500 of an impact of a notification with a time relationship between a notification and treatment. The x-axis represents a time relationship that increases from left to right and the y-axis represents an impact that increases from bottom to top. As shown in the graph 500, as the time relationship between when a notification is provided and a treatment is received increases, the impact decreases.

Figure 6:
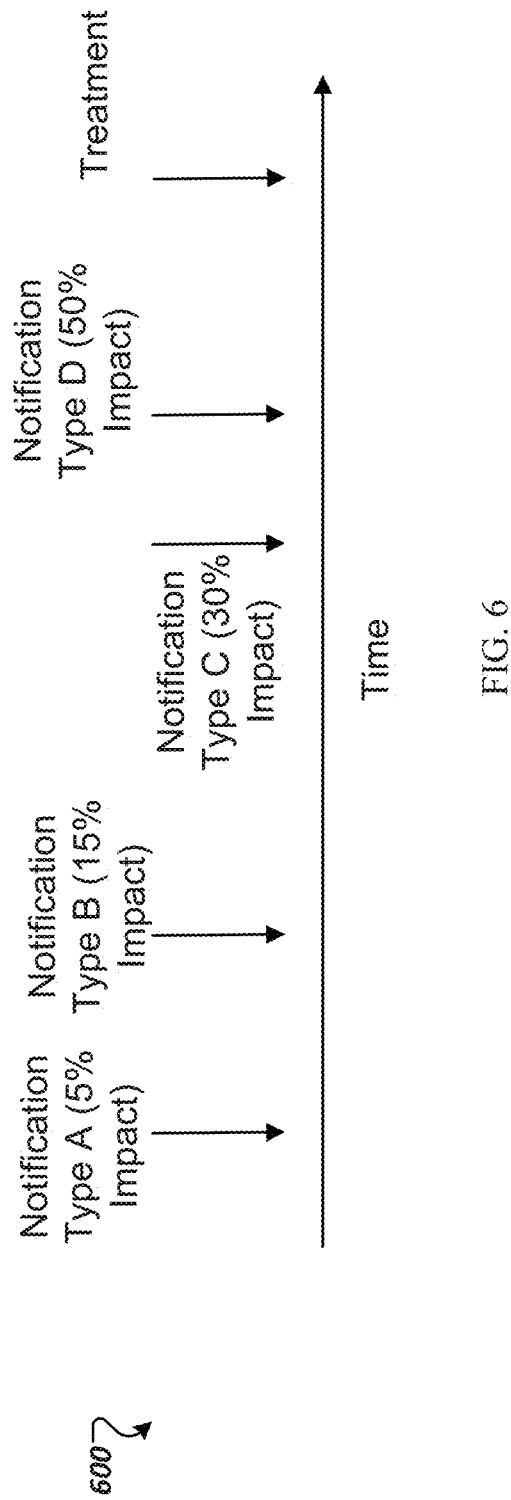
FIG. 6 illustrates a timeline of notifications and impacts.

FIG. 6 illustrates a timeline 600 of notifications and impacts. The timeline 600 shows how lower impacts are associated with notifications with greater time relationships. For example, notification type A that has the greatest time relationship is associated with an impact of 5%, notification type B which has a second greatest time relationship is associated with an impact of 15%, notification type C which has a third greatest time relationship is associated with an impact of 30%, and notification type D which has a least time relationship is associated with an impact of 50%.

Figure 7:
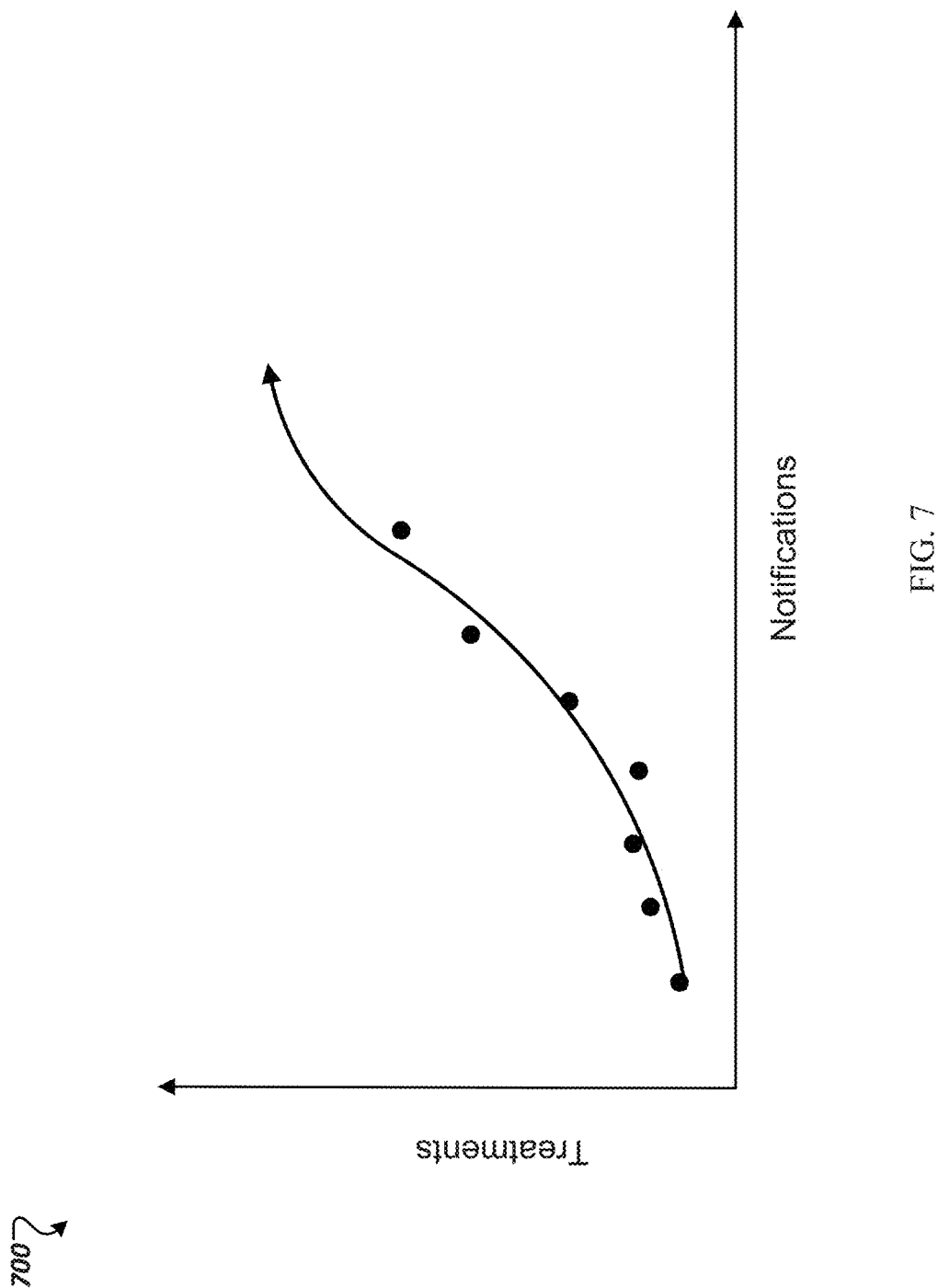
FIG. 7 illustrates an example graph output of a forecast model.

FIG. 7 illustrates an example graph 700 output of forecast model of number of treatments with number of notifications. The forecast model may be generated so that the graph 700 is fitted to numbers of notification provided indicated by notification data and numbers of treatments received indicated by the medical records.

Figure 8:
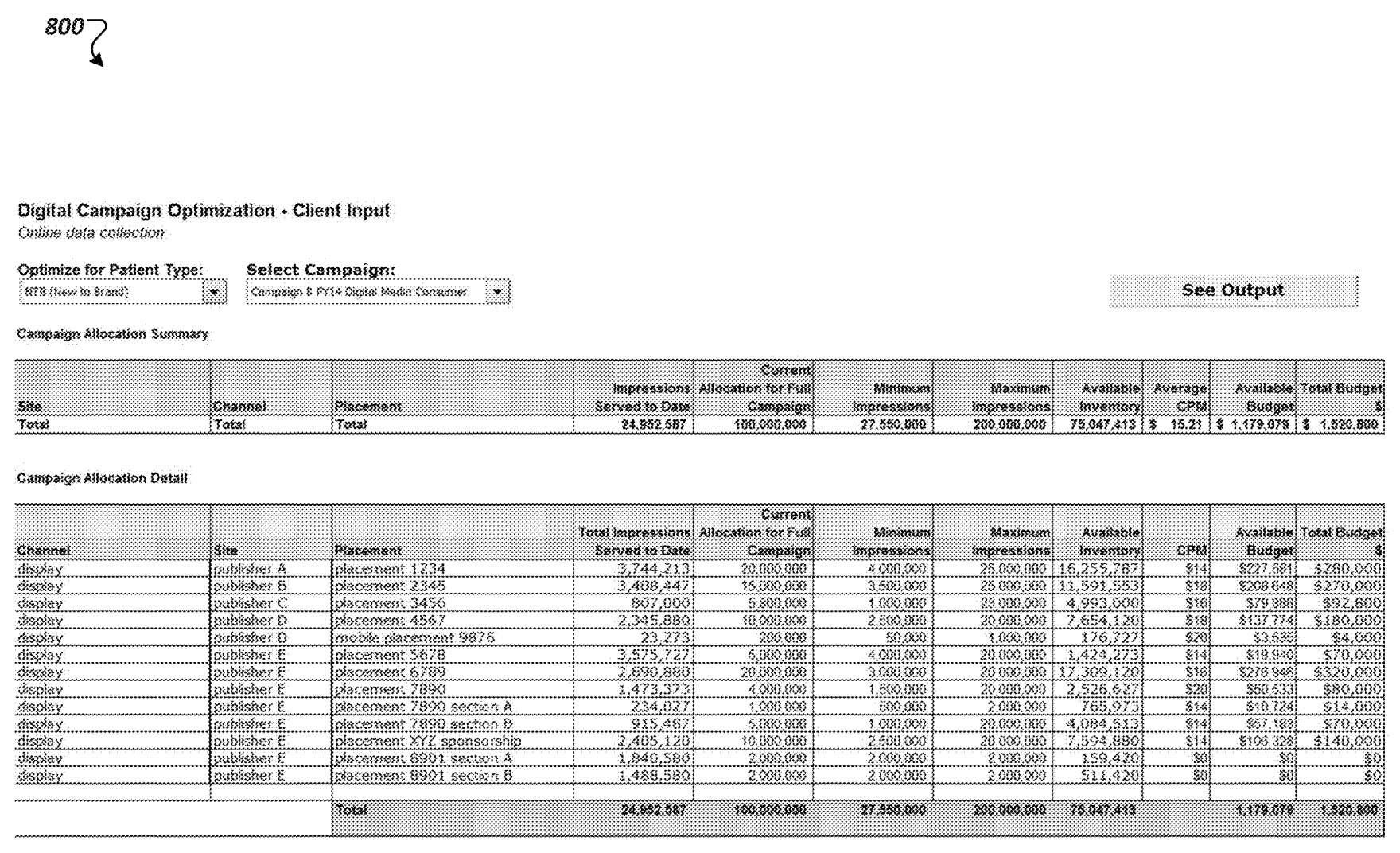

FIG. 8 illustrates an example user interface for receiving notification constraints for determining a plan for timely providing notifications. As shown in FIG. 8, the user interface may enable users to view and specify types of notifications differentiated by channel, e.g., display, audio, video, or some other channel, site providing the notification, e.g., publishers A-E, and placement of the notification, e.g., where on a site the notification may be provided. The user interface may further enable users to view and specify budgets for each type of notification, a total budget, minimum and maximum notifications to provide for each type of notification, and cost for each type of notification.

Figure 10:
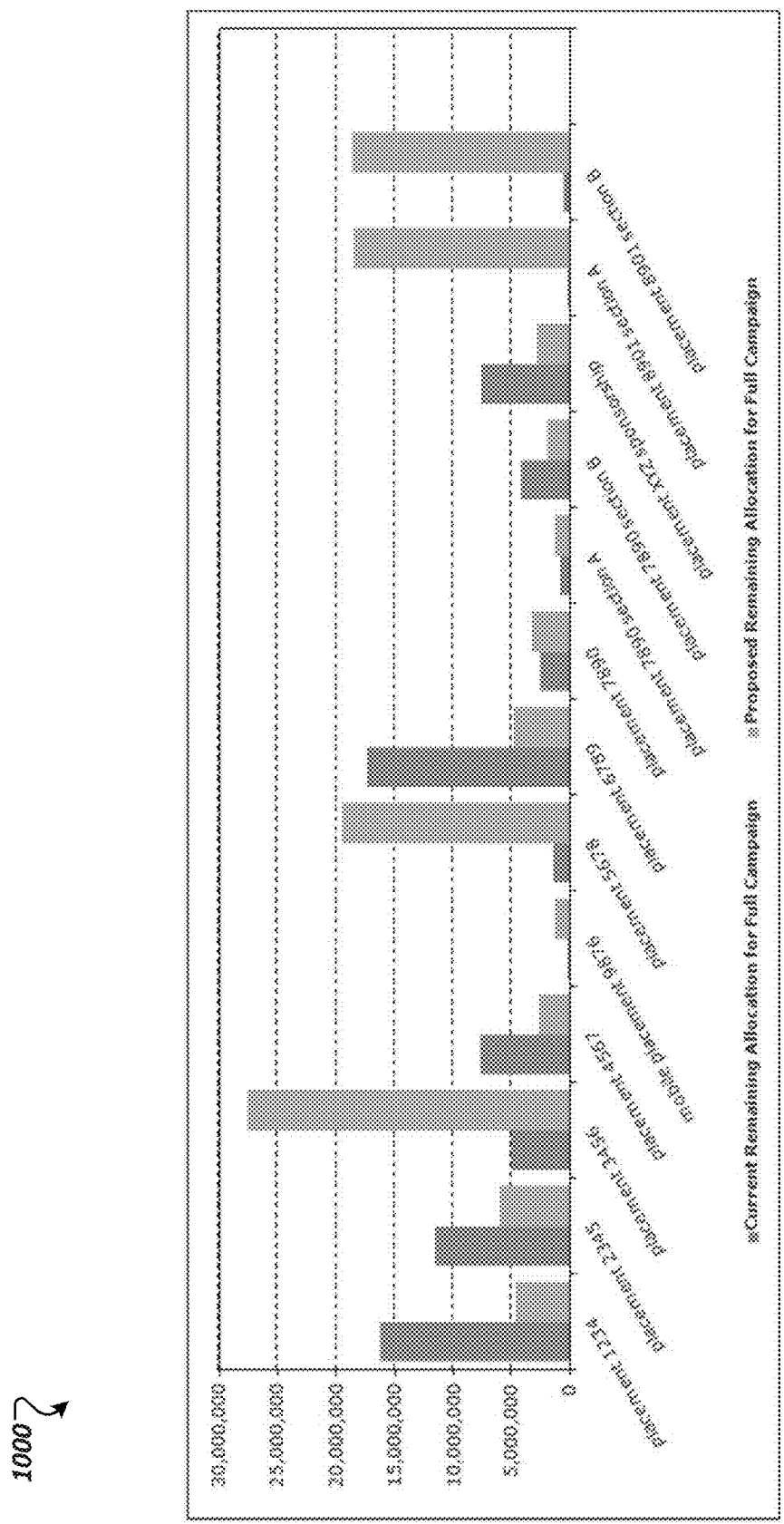

FIGS. 9 and 10 illustrate example plans 900, 1000 for timely providing notifications. As shown, the plans may indicate a number of each type of notification to provide to increase a number of patients receiving a treatment. The plans may further indicate an estimated budget used, an estimated number of notifications that will be used, and an estimated number of treatments that will be received, and differences from a previous plan.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method comprising:
   identifying a set of notifications, wherein:
      a recipient received a notification,
      an anonymized patient received a treatment,
      the recipient patient based on (i) a set of first identifiers for a set of anonymized patients and (ii) a set of second identifiers for a set of recipients;
   determining a set of time relationships between a set of treatments that were received by the set of anonymized patients and the set of notifications;
   training a time decay model to identify, for each time relationship in the set of time relationships, a set of coefficients for a decay function representing an impact of the notification on the corresponding treatment relative to the time relationship;
   computing, based on the set of coefficients and for each notification in the set of notifications, a score representing a likelihood that the notification being provided to the recipient impacted the corresponding treatment being received by the anonymized patient;
   determining a notification plan for notifying potential patients of treatments based on the scores for each notification included in the set of notifications, wherein the notification plan is determined to increase a number of treatments to be subsequently received by the anonymized patients; and
   scheduling the notifications based on the notification plan.

2. The method of claim 1, comprising:
   determining a forecast model based on scores computed for the set of notifications, where the forecast model stores, for each type of notification from among the set of notifications, a notification type label that is indicative of a relationship between a number of anonymized patients receiving the treatment and a number of recipients receiving notifications for the treatment.

3. The method of claim 2, comprising:
   scheduling notifications based on the forecast model.

4. The method of claim 1, wherein identifying the set of notifications comprises:
   determining that a second identifier for the recipient that received the notification and a first identifier for the anonymized patient that received the treatment both refer to the same person.

5. The method of claim 1, wherein determining time relationships between the treatments that were received by the set of anonymized patients and the notifications that were received by the set of recipients comprises:
   determining a first time when a treatment was received by a particular anonymized patient;

determining a second time when a notification for the treatment was received by a particular recipient corresponding to the particular anonymized patient; and determining a time relationship that represents a time length between the first time and the second time.

6. The method of claim 1, comprising:

determining for a particular patient that a first notification for the treatment was received by the particular patient and a second notification for the treatment was received by the particular patient.

7. The method of claim 1, wherein computing, based on the set of coefficients and for each notification included in the set of notifications, a score representing a likelihood that the notification being provided to the recipient impacted the corresponding treatment being received by the anonymized patient comprises:

generating an impact model by applying a random survival forest analysis to the set of coefficients.

8. The method of claim 7, wherein the impact model represents an impact of a notification on a treatment being received exponentially decayed from time when the notification was initially provided to a patient to a time the treatment was received by the patient.

9. The method of claim 1, further comprising:

determining an impact for a first notification to a recipient through a first type of notification based on a time relationship for the first notification; and determining an impact for a second notification to the recipient through a second type of notification based on a time relationship for the second notification.

10. The method of claim 1, further comprising:

aggregating impacts of a particular type of notification on a treatment being received over each anonymized patient included in the set of anonymized patients.

11. The method of claim 2, wherein determining a forecast model based on scores computed for the set of notifications, where the forecast model stores, for each type of notification from among the set of notifications, a notification type label that is indicative of a relationship between a number of anonymized patients receiving the treatment and a number of recipients receiving notifications for the treatment comprises:

determining, for each type of notification from among the set of notifications, a curve fitting a number of anonymized patients that previously received the treatment with a number of notifications previously provided to the set of recipients.

12. The method of claim 2, wherein determining a forecast model based on scores computed for the set of notifications, where the forecast model stores, for each type of notification from among the set of notifications, a notification type label that is indicative of a relationship between a number of anonymized patients receiving the treatment and a number of recipients receiving notifications for the treatment comprises:

determining the forecast model as a sigmoid function representing a diminishing effect of a number of notifications received by the set of recipients on a number of anonymized patients that receive the treatment.

13. The method of claim 2, wherein determining a forecast model based on scores computed for the set of notifications, where the forecast model stores, for each type of notification from among the set of notifications, a notification type label that is indicative of a relationship between a number of anonymized patients receiving the treatment and a number of recipients receiving notifications for the treatment comprises:

determining an initial forecast model for model patients based on the scores indicated by the impact model for the set of notifications; and projecting the initial forecast model to potential patients.

14. The method of claim 1, wherein determining the notification plan for notifying potential patients of treatments based on the scores for the notifications included in the set of notifications comprises:

receiving notification constraints for the notification plan;

determining that increasing a number of notifications for a particular channel increases a number of forecasted treatments to be received by anonymized patients included in the set of anonymized patients and satisfies the notification constraints; and determining a total number of notifications of each type that increases the number of forecasted treatments to be received by anonymized patients included in the set of anonymized patients.

15. The method of claim 3, wherein scheduling the notifications based on the notification plan comprises:

providing notifications for the treatment to the set of recipients.

16. The method of claim 1, wherein each anonymized patient included in the set of anonymized patients comprises a patient for which a patient identity cannot be determined but is distinguishable from other anonymized patients.

17. A computer system comprising one or more processors, configured to perform operations comprising:

identifying a set of notifications, wherein:
a recipient received a notification, an anonymized patient received a treatment,
the recipient corresponds to the anonymized patient based on (i) a set of first identifiers for a set of anonymized patients and (ii) a set of second identifiers for a set of recipients;

determining a set of time relationships between a set of treatments that were received by the set of anonymized patients and the set of notifications;

training a time decay model to identify, for each time relationship in the set of time relationships, a set of coefficients for a decay function representing an impact of the notification on the corresponding treatment relative to the time relationship;

computing, based on the set of coefficients and for each notification in the set of notifications, a score representing a likelihood that the notification being provided to the recipient impacted the corresponding treatment being received by the anonymized patient;

determining a notification plan for notifying potential patients of treatments based on the scores for each notification included in the set of notifications, wherein the notification plan is determined to increase a number of treatments to be subsequently received by the anonymized patients; and scheduling the notifications based on the notification plan.

18. A computer-readable medium, comprising software instructions, which when executed by a processor of a computer, causes the computer to perform operations comprising:

identifying a set of notifications, wherein:
a recipient received a notification,
an anonymized patient received a treatment,
the recipient corresponds to the anonymized patient based on (i) a set of first identifiers for a set of anonymized patients and (ii) a set of second identifiers for a set of recipients;

determining a set of time relationships between a set of treatments that were received by the set of anonymized patients and the set of notifications;

training a time decay model to identify, for each time relationship in the set of time relationships, a set of coefficients for a decay function representing an impact of the notification on the corresponding treatment relative to the time relationship;

computing, based on the set of coefficients and for each notification in the set of notifications, a score representing a likelihood that the notification being provided to the recipient impacted the corresponding treatment being received by the anonymized patient;

determining a notification plan for notifying potential patients of treatments based on the scores for each notification included in the set of notifications, wherein the notification plan is determined to increase a number of treatments to be subsequently received by the anonymized patients; and scheduling the notifications based on the notification plan.

* * * * *